(12) United States Patent
Härter et al.

(10) Patent No.: US 6,939,990 B2
(45) Date of Patent: *Sep. 6, 2005

(54) DERIVATIVES OF DICARBOXYLIC ACID HAVING PHARMACEUTICAL PROPERTIES

(75) Inventors: Michael Härter, Leverkusen (DE); Michael Hahn, Langenfeld (DE); Claudia Hirth-Dietrich, Wuppertal (DE); Andreas Knorr, Erkrath (DE); Elke Stahl, Bergisch Gladbach (DE); Johannes-Peter Stasch, Solingen (DE); Frank Wunder, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/469,557

(22) PCT Filed: Feb. 18, 2002

(86) PCT No.: PCT/EP02/01682

§ 371 (c)(1),
(2), (4) Date: Aug. 29, 2003

(87) PCT Pub. No.: WO02/070459

PCT Pub. Date: Sep. 12, 2002

(65) Prior Publication Data

US 2004/0110840 A1 Jun. 10, 2004

(30) Foreign Application Priority Data

Mar. 1, 2001 (DE) .......................... 101 09 859

(51) Int. Cl.[7] ............................... C07C 63/00
(52) U.S. Cl. ............... 562/405; 562/433; 562/442; 514/579
(58) Field of Search ............... 562/405, 433, 562/442; 514/579

(56) References Cited

U.S. PATENT DOCUMENTS 5,674,909 A 10/1997 Montanari et al. .......... 514/649

6,180,656 B1 1/2001 Furstner et al. .......... 514/406

FOREIGN PATENT DOCUMENTS

| CA | 2387107 | | 3/2001 |
| DE | 19943635 A1 | * | 3/2001 |
| WO | 9816223 | | 4/1998 |
| WO | 0119780 | | 3/2001 |
| WO | WO 0119780 | * | 3/2001 |

* cited by examiner

Primary Examiner—Cecilia J. Tsang
Assistant Examiner—Hector M. Reyes

(57) ABSTRACT

The invention relates to compounds of the general formula (I)

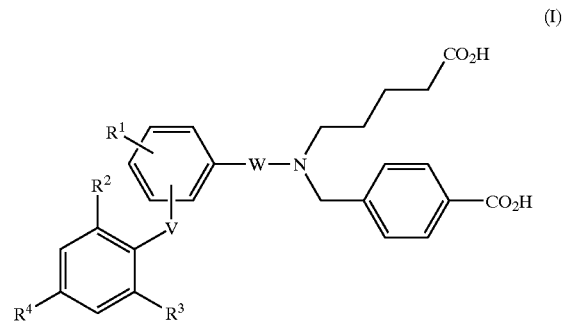

wherein $R^1$ represents H, halogen, or $OCF_3$; $R^2$ and $R^3$ each represents H or halogen; $R^4$ represents $C_{1-6}$-alkyl, $C_{3-8}$-cycloalkyl, $CF_3$, $OCF_3$, F, Cl, OMe, or optionally substituted phenyl; V represents O, $CH_2O$, $OCF_2$, or O—$C_{1-6}$-alkyl-O; and W represents $CH_2$ or $CH_2CH_2$. A process for making such compounds, pharmaceutical compositions containing them, and methods of treatment of various conditions using them are also disclosed and claimed.

12 Claims, No Drawings

DERIVATIVES OF DICARBOXYLIC ACID HAVING PHARMACEUTICAL PROPERTIES

The present invention relates to novel aminocarboxylic acid derivatives which stimulate soluble guanylate cyclase also via a novel mechanism of action which takes place without involvement of the heme group of the enzyme, to their preparation and to their use as medicaments, in particular as medicaments for treating cardiovascular disorders.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyze the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one heme per heterodimer, which is part of the regulatory center. The latter is of central importance for the mechanism of activation. NO is able to bind to the iron atom of heme and thus markedly increase the activity of the enzyme. Heme-free preparations cannot, by contrast, be stimulated by NO. CO is also able to attach to the central iron atom of heme, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in the neuronal signal transmission, and in disorders caused by an impairment of the aforementioned processes. Under pathophysiological conditions, the NO/cGMP system may be suppressed, which may lead for example to high blood pressure, platelet activation, increased cell proliferation, endothelial dysfunction, atherosclerosis, angina pectoris, heart failure, thromboses, stroke and myocardial infarction.

A possible way of treating such disorders which is independent of NO and aims at influencing the cGMP signal pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of heme. Besides the side effects, the development of tolerance is one of the crucial disadvantages of this mode of treatment.

Some substances which directly stimulate soluble guanylate cyclase, i.e. without previous release of NO, have been described in recent years, such as, for example, 3-(5'-hydroxymethyl-2'-furyl)-1-benzylindazole (YC-1, Wu et al., Blood 84 (1994), 4226; Mülsch et al., Br. J. Pharmacol. 120 (1997), 681), fatty acids (Goldberg et al, J. Biol. Chem. 252 (1977), 1279), diphenyliodonium hexafluorophosphate (Pettibone et al., Eur. J. Pharmcol. 116 (1985), 307), isoliquiritigenin (Yu et al., Brit. J. Pharmacol. 114 (1995), 1587) and various substituted pyrazole derivatives (WO 98/16223, WO 98/16507 and WO 98/23619).

The stimulators of soluble guanylate cyclase described above stimulate the enzyme either directly via the heme group (carbon monoxide, nitrogen monoxide or diphenyliodonium hexafluorophosphate) by interaction with the central iron of the heme group and a resulting change in conformation which leads to an increase in enzyme activity (Gerzer et al., FEBS Lett. 132(1981), 71), or via a heme-dependent mechanism which is independent of NO but leads to a potentiation of the stimulating action of NO or CO (for example YC-1, Hoenicka et al., J. Mol. Med. (1999) 14; or the pyrazole derivatives described in WO 98/16223, WO 98/16507 and WO 98/23619).

The stimulating action of isoliquiritigenin and of fatty acids, such as, for example, arachidonic acid, prostaglandin endoperoxides and fatty acid hydroperoxides on soluble guanylate cyclase claimed in the literature could not be confirmed (cf., for example, Hoenicka et al., J. Mol. Med. 77 (1999), 14).

If the heme group is removed from soluble guanylate cyclase, the enzyme still has detectable catalytic basal activity, i.e. cGMP is still being formed. The residual catalytic basal activity of the heme-free enzyme cannot be stimulated by any of the known stimulators mentioned above.

Stimulation of heme-free soluble guanylate cyclase by protoporphyrin IX has been described (Ignarro et al., Adv. Pharmacol. 26 (1994), 35). However, protoporphyrin IX can be considered to be a mimic of the NO-heme adduct, as a consquence of which the addition of protoporphyrin IX to soluble guanylate cyclase would be expected to result in the formation of a structure of the enzyme corresponding to heme-containing soluble guanylate cyclase stimulated by NO. This is also confirmed by the fact that the stimulating action of protoporphyrin IX is increased by the above-described NO-independent but heme-dependent stimulator YC-1 (Mülsch et al., Naunyn Schmiedebergs Arch. Pharmacol. 355, R47).

In contrast to the above-described compounds, known from the prior art as stimulators of soluble guanylate cyclase, the compounds according to the invention are capable of stimulating both the heme-containing and the heme-free form of soluble guanylate cyclase. Thus, in the case of these novel stimulators, stimulation of the enzyme is effected via a heme-independent path, and this is also confirmed by the fact that firstly the novel stimulators do not have any synergistic action with NO at the heme-containing enzyme and that secondly the action of these novel stimulators cannot be blocked by the heme-dependent inhibitor of soluble guanylate cyclase, i.e. 1H-1,2,4-oxadiazole-(4,3a)-quinoxalin-1-one (ODQ).

This is a novel therapeutic approach for treating cardiovascular disorders and other disorders accessible to therapy by influencing the cGMP signal pathway in organisms.

EP-A-0 345 068 describes, inter alia, the aminoalkanecarboxylic acid (1) as an intermediate in the synthesis of GABA antagonists:

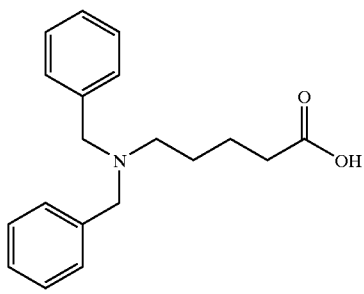

(1)

WO 93/00359 describes the aminoalkanecarboxylic acid (2) as an intermediate in peptide synthesis and its use as active compound for treating disorders of the central nervous system:

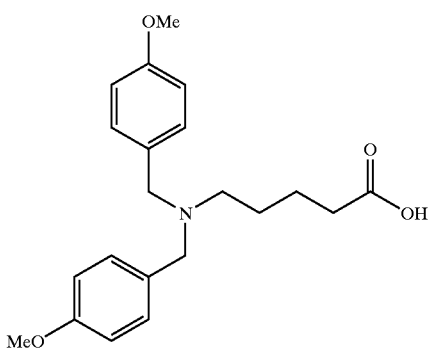

(2)

However, neither of these two publications describes that such aminoalkane-carboxylic acids may have a stimulating effect, independent of the heme group present in the enzyme, on soluble guanylate cyclase.

Substances having a structure similar to that of the compounds according to the invention are furthermore known from WO 01/19776, WO 01/19355, WO 01/19780 and WO 01/19778.

The present invention relates to compounds of the general formula (I)

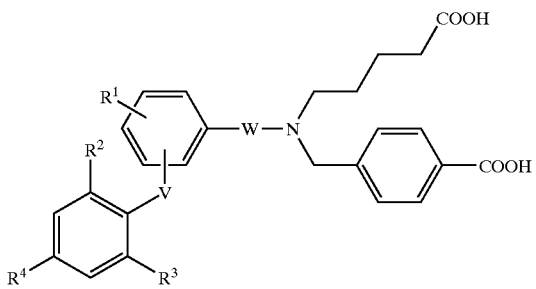

(I)

in which
$R^1$ is located in the meta- or para-position to the radical W and represents a radical from the group consisting of H, halogen and $OCF_3$;
$R^2$ represents H or halogen;
$R^3$ represents H or halogen;
$R^4$ represents $C_{1-6}$-alkyl, $C_{3-8}$-cycloalkyl, $CF_3$, $OCF_3$, F, Cl, OMe or phenyl, where the phenyl radical may additionally carry a substituent from the group consisting of halogen, CN, $C_{1-6}$-alkoxy, $CF_3$, $C_{1-6}$-alkyl;
V is located in the ortho- or meta-position to the radical W and represents O, $CH_2O$, $OCF_3$ or $O—C_{1-6}$-alkyl-O;
W represents $CH_2$ or $CH_2CH_2$;
and salts, isomers and hydrates thereof.

According to a preferred embodiment, the present invention relates to compounds of the formula (I) in which
$R^1$ is located in the meta-position to the radical W and represents a radical from the group consisting of H and halogen;
$R^2$ represents H or halogen;
$R^3$ represents H or halogen;
$R^4$ represents $C_{1-6}$-alkyl, $C_{3-8}$-cycloalkyl or phenyl, where the phenyl radical may additionally carry a substituent from the group consisting of halogen, CN, $C_{1-6}$-alkoxy, $CF_3$, $C_{1-6}$-alkyl;
V is located in the ortho- or meta-position to the radical W and represents O, $CH_2O$, $OCF_2$ or $O—C_{1-6}$-alkyl-O;
W represents $CH_2$ or $CH_2CH_2$;
and salts, isomers and hydrates thereof.

According to a particularly preferred embodiment, the present invention relates to compounds of the formula (I) in which
$R^1$ is located in the meta-position to the radical W and represents a radical from the group consisting of H, F, Cl and Br;
$R^2$ represents H,
$R^3$ represents H;
$R^4$ represents methyl, ethyl, n-propyl, i-propyl, n-butyl, i-butyl, t-butyl, cyclopropyl, cyclobutyl, cyclopentyl, cyclohexyl, or phenyl, where the phenyl radical may additionally carry a substituent from the group consisting of F, Cl, Br, CN, methoxy, ethoxy, n-propoxy, i-propoxy, n-butyloxy, i-butyloxy, t-butyloxy, $CF_3$, methyl, ethyl, n-propyl, i-propyl, n-butyl, i-butyl, t-butyl;
V is located in the ortho- or meta-position to the radical W and represents O, $CH_2O$, $OCF_2$ or $O—C_{1-6}$-alkyl-O;
W represents $CH_2$ or $CH_2CH_2$;
and salts, isomers and hydrates thereof.

According to a further particularly preferred embodiment, the present invention relates to compounds of the formula (I) in which
$R^1$ is located in the meta-position to the radical W and represents H;
$R^2$ represents H;
$R^3$ represents H;
$R^4$ represents cyclopropyl, cyclobutyl, cyclopentyl, cyclohexyl, or phenyl, where the phenyl radical may additionally carry a substituent from the group consisting of F, Cl, Br, $CF_3$;
V is located in the meta-position to the radical W and represents O;
W represents $CH_2$;
and salts, isomers and hydrates thereof.

According to a further particularly preferred embodiment, the present invention relates to compounds of the formula (I) in which
$R^1$ is located in the meta-position to the radical W and represents H;
$R^2$ represents H;
$R^3$ represents H;

$R^4$ represents phenyl, where the phenyl radical may additionally carry a substituent from the group consisting of F, Cl, Br, OMe, $CF_3$, methyl, ethyl, n-propyl, i-propyl, n-butyl, i-butyl, t-butyl;

V is located in the ortho-position to the radical W and represents $OCF_2$;

W represents $CH_2CH_2$;

and salts, isomers and hydrates thereof.

According to a further particularly preferred embodiment, the present invention relates to compounds of the formula (I) in which $R^1$ is located in the meta-position to the radical W and represents a radical from the group consisting of H, F, Cl and Br;

$R^2$ represents H;

$R^3$ represents H;

$R^4$ represents methyl, ethyl, n-propyl, i-propyl, n-butyl, i-butyl, t-butyl, cyclopropyl, cyclobutyl, cyclopentyl, cyclohexyl, or phenyl, where the phenyl radical may additionally carry a substituent from the group consisting of F. Cl, Br, CN, OMe, $CF_3$, methyl, ethyl, n-propyl, i-propyl, n-butyl, i-butyl, t-butyl;

V is located in the ortho-position to the radical W and represents $CH_2O$;

W represents $CH_2CH_2$;

and salts, isomers and hydrates thereof.

The compounds according to the invention of the general formula (I) may also be in the form of their salts. Mention may generally be made here of salts with organic or inorganic bases or acids.

Physiologically acceptable salts are preferred for the purposes of the present invention. Physiologically acceptable salts of the compounds according to the invention may be salts of the substances according to the invention with mineral acids, carboxylic acids or sulfonic acids. Particularly preferred examples are salts with hydrochloric acid, hydrobromic acid, sulfuric acid, phosphoric acid, methanesulfonic acid, ethanesulfonic acid, p-toluenesulfonic acid, benzenesulfonic acid, naphthalenedisulfonic acid, acetic acid, propionic acid, lactic acid, tartaric acid, citric acid, fumaric acid, maleic acid or benzoic acid.

Physiologically acceptable salts may likewise be metal or ammonium salts of the compounds according to the invention having a free carboxyl group. Particularly preferred examples are sodium, potassium, magnesium or calcium salts, and ammonium salts derived from ammonia, or organic amines, such as, for example, ethylamine, di- or triethylamine, di- or triethanolamine, dicyclohexylamine, dimethylaminoethanol, arginine, lysine or ethylenediamine.

The compounds according to the invention may exist in stereoisomeric forms which are either like image and mirror image (enantiomers), or not like image and mirror image (diastereomers). The invention relates both to the enantiomers or diastereomers and to their respective mixtures. The racermic forms, like the diastereomers, can be separated into the stereoisomerically uniform components in a known manner, for example by optical resolution or chromatographic separation. Double bonds present in the compounds according to the invention can be in the cis or trans configuration (Z or E form).

For the purposes of the present invention, the substituents are, unless defined otherwise, generally as defined below:

Alkyl generally represents a straight-chain or branched hydrocarbon radical having 1 to 20 carbon atoms. Examples which may be mentioned are methyl, ethyl, propyl, isopropyl, butyl, isobutyl, pentyl, isopentyl, hexyl, isohexyl, heptyl, isoheptyl, octyl and isooctyl, nonyl, decyl, dodeyl, eicosyl.

Alkoxy generally represents a straight-chain or branched hydrocarbon radical having 1 to 14 carbon atoms which is attached via an oxygen atom. Examples which may be mentioned are methoxy, ethoxy, propoxy, isopropoxy, butoxy, isobutoxy, pentoxy isopentoxy, hexoxy, isohexoxy, heptoxy, isoheptoxy, octoxy or isooctoxy. The terms "alkoxy" and "alkyloxy" are used synonymously.

Cycloalkyl generally represents a cyclic hydrocarbon radical having 3 to 8 carbon atoms. Preference is given to cyclopropyl, cyclopentyl and cyclohexyl. Cyclopentyl, cyclohexyl, cycloheptyl and cyclooctyl may be mentioned by way of example.

Halogen, for the purposes of the invention, represents fluorine, chlorine, bromine and iodine.

For the purposes of the present invention, the definitions of the radical V are to be understood as meaning that the atom mentioned first is attached to the phenyl ring which also carries the radical $R^1$. That is, in the case of $V=OCF_2$, the oxygen atom is attached to the phenyl ring which also carries the radical $R^1$.

The present invention furthermore relates to a process for preparing the compounds of the formula (I), characterized in that compounds of the formula (II)

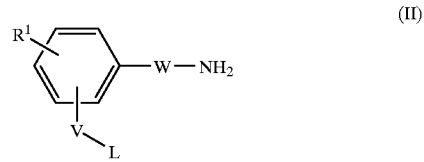

in which $R^1$, V and W are as defined in claim 1 and

L, if V is O, represents methyl or otherwise represents a radical of the formula

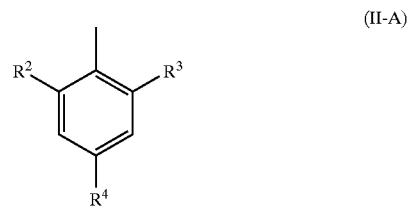

where $R^2$, $R^3$ and $R^4$ are as defined above, are reacted with a $C_{1-6}$-alkyl 4-formylbenzoate in an organic solvent, if appropriate with heating and simultaneous or subsequent addition of a reducing agent, to give compounds of the formula (III)

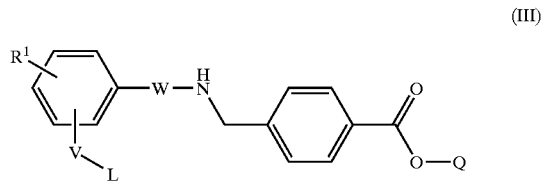

in which $R^1$, V, W and L are as defined above and Q represents a $C_{1-6}$-alkyl radical, then—if appropriate with prior cleavage of the ether to give the free hydroxyl group, if V represents O and L represents methyl—reacted with a $C_{1-6}$-alkyl ω-halovalerate in an organic solvent in the presence of a base with heating to give compounds of the formula (IV)

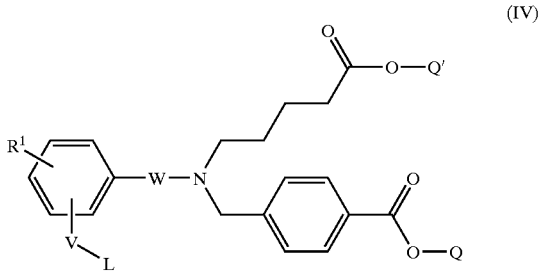

(IV)

in which $R^1$, V, W, and Q are as defined above, Q' represents a $C_{1-6}$-alkyl radical and L represents H—if V is O—or a radical of the formula II-A,
then—if V is O and L represents H—reacted with a compound of the formula IV-A in an organic solvent with heating

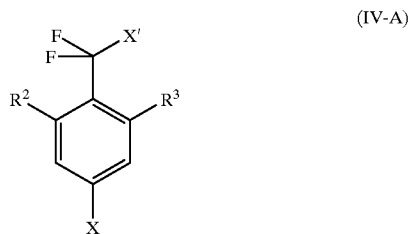

(IV-A)

where $R^2$ and $R^3$ are as defined in claim 1 and X and X' each represent halogen,
followed by palladium-catalyzed substitution of the radical X with a benzene boronic acid derivative to give compounds of the formula (V)

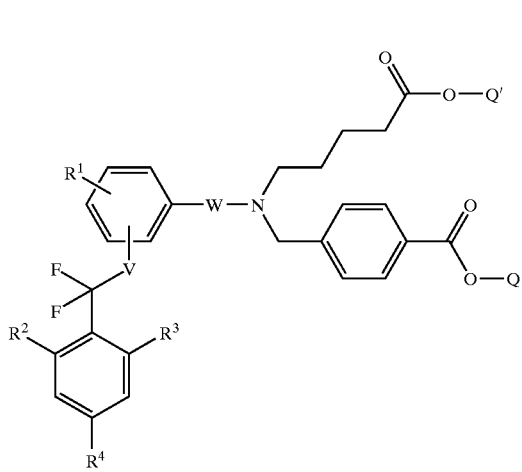

(V)

and subsequent hydrolysis of the compounds of the formula (IV) or (V) under alkaline conditions to give the compounds of the formula (I).

The bases which are preferably used for the processes according to the invention include basic compounds which are customarily used for basic reactions. Preference is given to using alkali metal hydrides, such as, for example, sodium hydride or potassium hydride, or alkali metal alkoxides, such as sodium methoxide, sodium ethoxide, potassium methoxide, potassium ethoxide or potassium t-butoxide, or carbonates, such as sodium carbonate, cesium carbonate or potassium carbonate, or amides, such as sodium amide or lithium diisopropylamide, or organolithium compounds, such as phenyllithium, butyllithium or methyllithium, or sodium hexamethyldisilazane.

Solvents which are preferred for converting the compounds of the formula (II) into the compounds of the formula (III) are customary organic solvents which do not change under the reaction conditions. Preference is given to using, for the process according to the invention, ethers, such as diethyl ether, butyl methyl ether, dioxane, tetrahydrofuran, glycol dimethyl ether or diethylene glycol dimethyl ether, or hydrocarbons such as benzene, toluene, xylene or petroleum ether, or alcohols, such as methanol or ethanol, or halogenated hydrocarbons, such as carbon tetrachloride, chloromethane or dichloromethane. It is, of course, also possible to use mixtures of the solvents mentioned above. Preference according to the invention is given to using ethanol, methanol, dichloromethane or toluene.

Initially, the compounds of the formula (II) are reacted with a $C_{1-6}$-alkyl 4-formylbenzoate to give a Schiff base, which is then reduced with customary reducing agents, such as, for example, $NaBH_4$, $H_2$/Pd/C, etc., or reacted directly under the conditions of a reductive alkylation in the presence of a reducing agent, such as, for example, $H_2$/Pd/C, $NaCNBH_3$, $NaH(OAc)_3$ (cf. Patai, Ed., The Chemistry of the Carbon-Nitrogen Double Bond, pp. 276–293 and the literature cited therein). Here, depending on the nature of the starting material, the reaction can be carried out at room temperature or has to be heated at from 50 to 110° C. for several hours up to several days. The reaction can be carried out at atmospheric pressure, elevated or reduced pressure (for example in the range of from 0.5 to 5 bar). In general, the reaction is carried out at atmosphere pressure. $C_{1-6}$-Alkyl 4-formylbenzoates are commercially available, known from the literature, or can be synthesized analogously to processes known from the literature (cf., for example, J. Med. Chem. 1989, 32, 1277; Chem. Ber. 1938, 71, 335; Bull. Soc. Chim. Fr. 1996, 123, 679, WO 96/11902; DE-2209128; Synthesis 1995; 1135; Bull. Chem. Soc. Jpn. 1985, 58, 2192, Synthesis 1983, 942; J. Am. Chem. Soc. 1992, 114, 8158).

The conversion of the compounds of the formula (III) into the compounds of the formula (IV) can preferably be carried out in acetonitrile or butyronitrile, in each case by reacting the compounds (II) and (III), (IV) and (V) and (VI) and (VII), respectively, in the presence of a base, such as sodium carbonate, $Et_3N$, DABCO, $K_2CO_3$, KOH, NaOH or NaH. In general, the reaction can be carried out in a temperature range of from −20° C. to +90° C., preferably from 0° C. to +70° C. The reaction can be carried out at atmospheric pressure, elevated or reduced pressure (for example in a range of from 0.5 to 5 bar). In general, the reaction is carried out at atmospheric pressure. However, suitable solvents are, in principle, the solvents mentioned above for the conversion of the compounds of the formula (II) into compounds of the formula (III). According to the invention, the alkyl ω-halovalerate used is preferably the corresponding methyl ω-bromovalerate. Alkyl ω-halovalerates are commercially available, known from the literature or can be synthesized according to processes known from the literature (cf., for example, J. Chem. Soc. 1958, 3065).

If V is O and L is methyl, the methoxy group present should be converted into the free hydroxyl group prior to the reaction of the corresponding compound of the formula (II) with the alkyl ω-halovalerate. This can be carried out in a known manner (cf., for example, T. W. Greene, P. G. M. Wuts, Protective Groups in Organic Synthesis, second edition, New York, 1991). The methyl group can be removed with formation of the phenol, for example, using boron tribromide in methylene chloride at from −70 to 20° C., using trimethylsilyl iodide in chloroform at 25–50° C. or using sodium ethylthiolate in DMF at 150° C. According to the invention, the reaction with boron tribromide is preferred.

The compounds of the formula (IV) are then converted into the compounds of the formula (I) by hydrolysis of the ester functions, giving the free carboxyl groups, for example by addition of aqueous solutions of strong acids, such as, for example, HCl or $H_2SO_4$, or strong bases, such as, for example, NaOH, KOH or LiOH. The reaction can be carried out in one of the organic solvents mentioned above, in water or in mixtures of organic solvents or mixtures of organic solvents with water. Preference according to the invention is given, for example, to carrying out the reaction in a mixture of water and methanol or dioxane. The reaction can generally be carried out in a temperature range of from −20° C. to +90° C., preferably of from 0° C. to +90° C. The reaction can be carried out under atmospheric pressure, elevated or reduced pressure (for example in a range of from 0.5 to 5 bar). In general, the reaction is carried out under atmospheric pressure.

If, in the compounds of the formula (IV), V is O and L is H, the hydrolysis of the ester functions described above is preceded by a reaction with the compounds of the formula (IV-A). This is a nucleophilic substitution of a leaving group X' in the compound of the formula (IV-A) by the hydroxyl function of the compound of the formula (IV). Suitable leaving groups X' are, for example: halogen, tosylate, mesylate or a hydroxyl function activated by reagents such as diisopropyl azodicarboxylate/$PPh_3$ (Mitsonobu reaction). Preferably, X' is halogen, particularly preferably Br. This reaction can preferably be carried out in dimethylformamide (DMF) by reacting the compounds (IV) and (IV-A) in the presence of a base, such as sodium carbonate, potassium carbonate, $Et_3N$, DABCO, $K_2CO_3$, KOH, NaOH or preferably NaH. The reaction can generally be carried out in a temperature range of from −20° C. to +90° C., preferably of from 0° C. to +90° C. The reaction can be carried out under atmospheric pressure, elevated or reduced pressure (for example in a range of from 0.5 to 5 bar). In general, the eraction is carried out under atmospheric pressure.

The compounds of the formula (IV-A) can be obtained from compounds which are commercially available, known from the literature or synthesizable analogously to processes known from the literature (cf., for example, J. prakt. Chem. 1960, 341; Farmaco Ed. Sci. 1956, 378; Eur. J. Med. Chim. Ther. 1984, 19, 205; Bull. Soc. Chim. Fr. 1951, 97. Liebigs Ann. Chem. 1954, 586, 52; EP-A-0 334 137) by NBS bromination of the difluoromethyl group analogously to processes known from the literature (cf., for example, Monatsh. Chem. 1996, 127(2), 201–217; J. Med. Chem. 1992, 35, 368; J. heterocycl. Chem. 24 (1987), N3, 725–731; Synth. Commun. 1996, 26(15), 2803–2809).

The resulting compound, which contains a substitutable group X, is then prepared by reaction with a benzeneboronic acid derivative in the presence of a palladium compound and, if appropriate, a reducing agent and further additives in basic medium. Formaly, the reaction is a reductive coupling as described, for example, in L. S. Hegedus, Organometallics in Synthesis, M. Schlosser, Ed., Wiley & Sons, 1994. The substitutable group X used can, for example, be a halogen radical, such as Br or I, or a customary leaving group, such as, for example, a triflate radical. Preference according to the invention is given to a halogen radical, in particular to Br. The palladium compound used can be a palladium (II) compound, such as, for example, $Cl_2Pd(PPh_3)_2$ or $Pd(OAc)_2$, or a palladium(0) compound, such as, for example, $Pd(PPh_3)_4$ or $Pd_2(dba)_3$. If required, a reducing agent, such as, for example, triphenylphosphine, or other additives, such as, for example, Cu(I)Br, $NBu_4NCl$, LiCl or $Ag_3PO_4$, can additionally be added to the reaction mixture (cf. T Jeffery, Tetrahedron lett. 1985, 26, 2667–2670; T. Jeffery, J. Chem. Soc. Chem. Commun. 1984, 1287–1289; S. Bräse, A. deMejiere in "Metal-catalyzed cross-coupling reactions", Ed. F. Diederich, P. J. Stang, Wiley-VCH, Weinheim 1998, 99–166). The reaction is carried out in the presence of a customary base, such as, for example, $Na_2CO_3$, NaOH or triethylamine. Suitable solvents are the organic solvents mentioned above, ethers, such as, for example, 1,2-dimethoxyethane, being particularly preferred. In general, the reaction can be carried out in a temperature range of from −20° C. to +90° C., preferably of from 0° C. to +90° C. The reaction can be carried out under atmospheric pressure, elevated or reduced pressure (for example in a range of from 0.5 to 5 bar). In general, the reaction is carried out at atmospheric pressure.

Benzeneboronic acids are commercially available, known from the literature, or can be synthesized analogously to processes known from the literature (cf., for example, J. Chem. Soc. C 1966, 566. J. Org. Chem., 38, 1973, 4016).

The compounds of the formula (V) prepared in this manner can then be hydrolyzed as described above to give the compounds of the formula (I).

The compounds of the formula (II) are obtainable by different routes or may even be commercially available. Thus, compounds of the formula (II) where V is $CH_2O$ can be obtained by esterifying commercially available methylbenzoic acids, NBS bromination of the methyl group analogously to processes known from the literature (cf., for example, Manatsh. Chem. 1996, 127(2). 201–217; J. Med. Chem. 1992, 35, 368; J. heterocycl. Chem. 24 (1987), N3, 725–731; Synth. Commun. 1996, 26(15), 2803–2809) to give the corresponding bromomethyl compounds, subsequent substitution of the bromine group introduced by the phenolic OH group of a commercially available phenol compound in an organic solvent, such as acetonitrile, in the presence of a base, such as, for example, potassium carbonate, and conversion of the ester group by reduction with customary reducing agents, such as, for example, $LiAlH_4$, conversion into the corresponding benzyl halide using, for example, $SOCl_2$ or using carbon tetrabromide/triphenylphosphine in an organic solvent, such as diethyl ether, nucleophilic substitution with a cyanide, such as, for example, NaCN or trimethylsilyl cyanide, and reduction of the nitrile function by methods known from the literature, such as, for example, $BH_3.THF$, $BH_3.S(CH_3)_2$ or $LiAlH_4/AlCl_3$.

If V is O, the compounds of the formula (II) can be prepared from halobenzonitriles which are commercially available known from the literature or synthesizable analogously to processes known from the literature (cf., for example, Chem. Pharm. Bull. 31, 10, 1983, 3424–3445; Bull. Chem. Soc. Fr. <II>, 1979, 241–248; Chem. Ber. 80, 1947, 469–472, J. Chem. Soc. 1933, 489–493) by reaction with a commercially available phenol compound in an organic solvent, such as pyridine, in the presence of a base, such as, for example, potassium carbonate, and in the presence of CuI, under an atmosphere of protective gas and with heating, followed by reduction of the nitrile function as described above.

The compounds of the general formula (I) according to the invention show a valuable range of pharmacological effects which could not have been predicted.

The compounds of the general formula (I) according to the invention, bring about vasorelaxation and an inhibition of platelet aggregation and lead to a reduction in blood pressure and an increase in the coronary blood flow. These effects are mediated by direct stimulation of soluble guanylate cyclase and an intracellular increase in cGMP.

They can therefore be employed in medicaments for the treatment of cardiovascular disorders such as, for example, for the treatment of high blood pressure and heart failure, stable and unstable angina pectoris, peripheral and cardiac vascular disorders, of arrhythmias, for the treatment of thromboembolic disorders and ischemias such as myocardial infarction, stroke, transitory and ischemic attacks, disturbances of peripheral blood flow, prevention of restenosis such as after thrombolysis therapies, percutaneous transluminal angioplasties (PTAs), percutaneous transluminal coronary angioplasties (PTCAs), bypass and for the treatment of arteriosclerosis, fibrotic disorders, such as fibrosis of the liver or pulmonary fibrosis, asthmatic disorders and diseases of the urogenital system such as, for example, prostate hypertrophy, erectile dysfunction, female sexual dysfunction and incontinence and also for the treatment of glaucoma.

The compounds of the general formula (I) described in the present invention, are also active compounds suitable for controlling central nervous system diseases characterized by disturbances of the NO/cGMP system. They are suitable in particular for removing cognitive deficits, for improving learning and memory performances and for treating Alzheimer's disease. They are also suitable for treating disorders of the central nervous system such as states of anxiety, tension and depression, CNS-related sexual dysfunctions and sleep disturbances, and for controlling pathological disturbances of the intake of food, stimulants and addictive substances.

The active compounds are furthermore also suitable for regulating cerebral blood flow and thus represent effective agents for controlling migraine.

They are also suitable for the prophylaxis and control of the sequelae of cerebral infarction (apoplexia cerebri) such as stroke, cerebral ischemias and craniocerebral trauma. The compounds according to the invention of the general formula (I) can likewise be employed for controlling states of pain.

In addition, the compounds according to the invention have an anti-inflammatory effect and can therefore be employed as anti-inflammatory agents.

As a particular and surprising feature, the compounds of the present invention have a long duration of action, which was unexpected.

Vasorelaxant Effect In Vitro

Rabbits are anesthetized or killed by intravenous injection of thiopental sodium (about 50 mg/kg) and exsanguinated. The arteria saphena is removed and divided into rings 3 mm wide. The individual rings are in each case mounted on a pair of hooks of triangular shape, open at the end and made of special wire (Remanium®) having a diameter of 0.3 mm. Under pretension, each ring is introduced into a 5 ml organ bath containing carbogen-gassed Krebs-Henseleit solution at 37° C. with the following composition (mM): NaCl: 119; KCl: 4.8; $CaCl_2 \times 2H_2O$: 1; $MgSO_4 \times 7H_2O$: 1.4; $KH_2PO_4$: 1.2; $NaHCO_3$: 25; glucose: 10; bovine serum albumin: 0.001%. The force of contraction is detected with Statham UC2 cells, amplified and digitized via A/D converters (DAS-1802 HC, Keithley Instruments, Munich) and recorded in parallel on chart recorders. Contractions are generated by adding phenylephrine.

After several (generally 4) control cycles, the substance to be investigated is added in each further run in increasing dosage in each case, and the height of the contraction reached under the influence of the test substance is compared with the height of the contraction reached in the last preceding run. The concentration necessary to reduce the height of the control value by 50% ($IC_{50}$) is calculated from this. The standard application volume is 5 µl. The DMSO content in the bath solution corresponds to 0.1%.

The results are shown in table 1:

TABLE 1

| Vasorelaxant effect in vitro | |
|---|---|
| Example | $IC_{50}$ (nM) |
| 2 | 55 |
| 3 | 36 |
| 6 | 0.041 |
| 12 | 0.4 |
| 17 | 0.26 |

Stimulation of Recombinant Soluble Guanylate Cyclase (sGC) In Vitro

The investigations of the stimulation of recombinant soluble guanylate cyclase (sGC) and the compounds according to the invention with and without sodium nitroprusside and with and without the heme-dependent sGC inhibitor 1H-1,2,4-oxadiazole-(4,3a)-quinoxalin-1-one (ODQ) were carried out according to the method described in detail in the following literature reference: M. Hoenicka, E. M. Becker, H. Apeler, T. Sirichoke, H. Schroeder, R. Gerzer and J-P. Stasch: Purified soluble guanylyl cyclase expressed in a baculovirus/Sf9 system: stimulation by YC-1, nitric oxide, and carbon oxide. J. Mol. Med. 77 (1999): 14–23.

The heme-free guanylate cyclase was obtained by adding Tween 20 to the sample buffer (final concentration 0.5%).

Activation of sGC by a test substance is stated as n-fold stimulation of basal activity.

Investigation of the Antifibrotic Action of the Substances In Vivo

Method

The antifibrotic action of the substances was investigated using the model of the porcine serum-induced rat liver fibrosis. Treatment with heterologous serum, for example porcine serum in rats, is a method frequently used in the literature for inducing fibrosis of the liver with subsequent cirrhosis which, in contrast to other models, causes only minimal damage and inflammation of the parenchyma cells of the liver (Bhunchet, E. and Wake, K. (1992): Role of mesenchymal cell populations in porcine serum-induced rat liver fibrosis. Hepatology 16: 1452–1473). Female Sprague Dawley rats were treated 2× per week with 0.5 ml/animal of sterile porcine serum (Sigma) i.p., control animals were treated with sterile physiological saline (2× per week 0.5 ml/animal i.p.). The treatment with test substance (1× per day in 5 ml/kg of p.o. solvent comprising 20% Cremophor, 10% Transcutol and 70% $H_2O$) was carried out in parallel to the treatment with porcine serum. After seven weeks of treatment, the animals were killed and the livers were removed in order to quantify the collagen content.

For the histological examination of the liver tissue, standardized transverse tissue cylinders (about 10×2 mm) were punched out of the right anterior lobe of the liver. For the detection of scar collagen caused by liver fibrosis, frozen sections were stained with 0.1% strength Pikrosirius Red solution.

Fast Green was used as counterstain to enhance contrast. In each section, the extent of liver fibrosis was determined as a percentage of the area stained by Pikrosirius Red of the total area measured. The parameters of the video microscopic stain detection were standardized and kept constant for the entire experiment. 64 fields of a standardized grid of 31 mm² were measured using a final amplification of 100. For semiautomatic morphometry, a Leica Quantimed 500MC (Leica Germany) was used.

To determine OH-proline according to Prockop and Udenfried (Prockop, D. J. and Udenfried, S. A. (1960): A specific method for the analysis of hydroxyproline in tissues and urine. Anal. Biochem. 1: 228–239), in each case 50–100 mg of liver tissue were dried and boiled with 6N HCl for about 17 hours. The acid was evaporated in a vacuum drying oven and the residue was then dissolved in 5 ml of distilled water and filtered. 200 µl of the filtered solution were incubated at room temperature with 200 µl of ethanol and 200 µl of oxidation solution (7% strength aqueous chloramine T hydrate solution, diluted 1:4 with acetate/citrate buffer pH 6.0) for 25 min. 400 µl of Erlich's reagent (12 g of 4-dimethylaminobenzaldehyde in 20 ml of ethanol+2.74 ml of concentrated sulfuric acid in 20 ml of ethanol) were then added. After 3 hours of incubation at 35° C., absorption at 573 nm was measured. Aqueous OH-proline solutions (Sigma) were used for the calibration curve. The OH-proline content of the liver samples was calculated in mg per g of liver dry weight.

Results

The OH-proline values agreed very well with the results of the morphometric fibrosis measurement: without simultaneous administration of substance, the porcine serum treatment resulted in a pronounced accumulation of collagen in the liver. The formation of these collagen deposits is reduced by treatment with the substances in a dose-dependent manner.

The present invention includes pharmaceutical preparations which, in addition to non-toxic, inert, pharmaceutically acceptable carriers, comprises the compounds according to the invention, in particular the compounds of the general formula (I), and processes for preparing these preparations.

The active compound, if appropriate in one or more of the carriers listed above, can also be present in microencapsulated form.

The therapeutically effective compounds, in particular the compounds of the general formula (I), should be present in the pharmaceutical preparations detailed above in a concentration of about 0.1 to 99.5, preferably of about 0.5 to 95, % by weight of the complete mixture.

The pharmaceutical preparations detailed above may, apart from the compounds according to the invention, in particular the compounds of the general formula (I), also contain other active pharmaceutical ingredients.

It has generally proved to be advantageous both in human and in veterinary medicine to administer the active compound(s) according to the invention in total amounts of about 0.5 to about 500, preferably 5 to 100, mg/kg of body weight every 24 hours, where appropriate in the form of a plurality of single doses, to achieve the desired results. A single dose contains the active compound(s) according to the invention preferably in amounts of about 1 to about 80, in particular 3 to 30, mg/kg of body weight.

Below, the present invention is illustrated in more detail using non-limiting preferred examples. Unless indicated otherwise, all quantities are stated in percent by weight.

EXAMPLES

Abbreviations:

| RT: | room temperature |
| EA: | ethyl acetate |
| BABA: | n-butyl acetate/n-butanol/glacial acetic acid/phosphate buffer pH 6 (50:9:25.15; org. phase) |

Mobile Phases for Thin-layer Chromatograhy:

| T1 E1: | toluene - ethyl acetate (1:1) |
| T1 EtOH1: | toluene - methanol (1:1) |
| C1 E1: | cyclohexane - ethyl acetate (1:1) |
| C1 E2: | cyclohexane - ethyl acetate (1:2) |

Starting Materials

Ex. I 3-(4-Cyclohexylphenoxy)benzonitrile

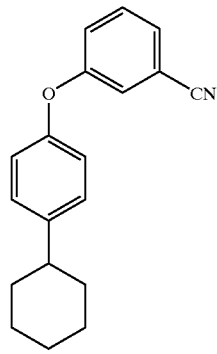

Under argon, 1.2 g (6.81 mmol) of 4-cyclohexylphenol, 7.44 g (40.85 mmol) of 3-bromobenzonitrile, 1.3 g (6.81 mmol) of copper(I) iodide and 1.88 g (13.62 mmol) of potassium carbonate are suspended in 24 ml of pyridine and stirred at 140° C. for 15 h. After cooling, the reaction mixture is filtered through kieselguhr, the filter cake is washed with dichloromethane and the filtrate is concentrated using a rotary evaporator. The resulting residue is taken up in ethyl acetate and water, and 2-N-HCl is added. The resulting precipitate is filtered off through kieselguhr. The resulting filtrate is then extracted twice with 2-N-HCl and with sat. NaCl solution. After drying over $MgSO_4$ and removal of the solvent by evaporation, the product is purified by column chromatography (silica gel, cyclohexane/ethyl acetate 25:1). This gives 876 mg (3.16 mmol, 44% yield) of a colorless oil.

$R_f$ (cyclohexane/ethyl acetate, 2:1): 0.71. $^1$H-NMR (300 MHz, $CDCl_3$, δ/ppm): 7.42–7.32 (2H, m), 7.29–7.15 (4H, m), 6.95 (2H, d), 2.35 (1H, m), 1.96–1.60 (5H, m), 1.50–1.25 (5H, m). MS (DCl, $NH_3$: 572 ($2M+NH_4^+$), 317 ($M+N_2H_7^+$), 295 ($M+NH_4^+$), 277 ($M^+$).

Ex. II

3-(4-Cyclohexylphenoxy)benzylamine

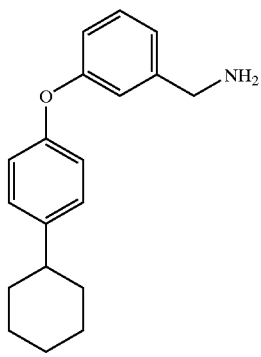

At 0° C., a solution of 600 mg (2.16 mmol) of 3-(4-cyclohexylphenoxy)benzonitrile from Ex. I in 6 ml of anhydrous diethyl ether is added dropwise to 4.32 ml (4.32 mmol) of a 1-molar solution of LiAlH$_4$ in THF. Over a period of 4 h, the reaction mixture is warmed to room temperature, and 10 ml of a sat. solution of NH$_4$Cl are then added carefully, the mixture is diluted with ether and the organic phase is removed. The organic phase is washed successively with water and a sat. solution of NaCl, dried over MgSO$_4$ and, after filtration, freed from the solvent. This gives 573 mg (1.81 mmol, purity 88.82%, 84% yield) of 3-(4-cyclohexylphenoxy)benzylamine.

R$_f$ (dichloromethane/methanol 9/1): 0.13 $^1$H-NMR (400 MHz, CDCl$_3$, δ/ppm): 7.26 (2H, d), 7.16 (2H, d), 7.05–6.85 (4H, m), 3.86 (2H, s), 2.51 (1H, m), 1.93–1.79 (4H, m), 1.70–1.55 (2H, m), 1.48–1.31 (4H, m). MS (EI): 280 (M$^+$).

Ex. III

Methyl 4-({[3-(4-cyclohexylphenoxy)benzyl]amino}methyl)benzoate

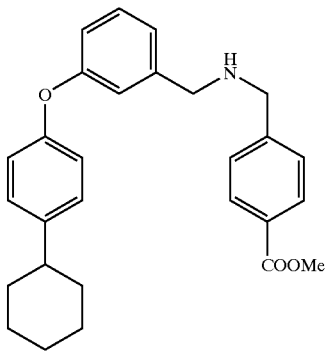

Under argon, 806 mg (3.80 mmol) of sodium triacetoxyborohydride are added to a solution of 535 mg (1.90 mmol) of 3-(4-cyclohexylphenoxy)benzylamine from Ex. II and 312 mg (1.90 mmol) of methyl 4-formylbenzoate in 5 ml of dichloromethane, and the mixture is stirred at room temperature overnight. 10 ml of a sat. solution of NaHCO$_3$ are then added carefully to the reaction mixture, the mixture is diluted with dichloromethane and the organic phase is removed. The organic phase is dried over MgSO$_4$ and concentrated using a rotary evaporator. This gives 429 mg (1 mmol) of methyl 4-({[3-(4-cyclohexylphenoxy)benzyl]amino}methyl)benzoate as a colorless oil.

R$_f$ (dichloromethane/methanol 10:1): 0.56. $^1$H-NMR (300 MHz CDCl$_3$, δ/ppm): 7.99 (2H, d), 7.40 (2H, d), 7.28 (1H, d), 7.18 (2H, d), 7.08–6.99 (2H, m), 6.97–6.87 (3H, m), 3.91 (3H, s), 3.85 (2H, s), 3.78 (2H, s), 2.51 (1H, m), 1.93–1.70 (5H, m), 1.50–1.32 (5H, m). MS (ESI): 430 (M+H$^+$).

Ex. IV

Methyl 4-{[[3-(4-cyclohexylphenoxy)benzyl](5-methoxy-5-oxopentyl)amino]methyl}benzoate

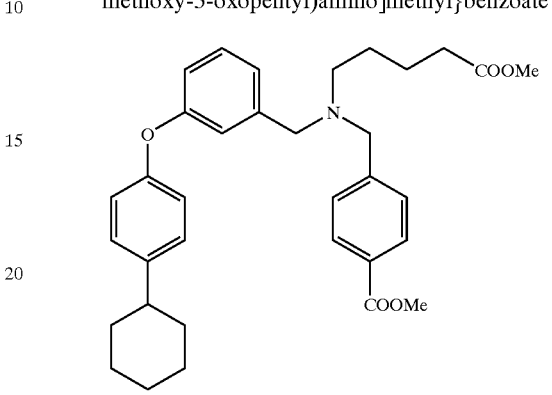

207 mg (1.95 mmol) of anhydrous potassium carbonate are added to a solution of 381 mg (0.89 mmol) of methyl 4-({[3-(4-cyclohexylphenoxy)benzyl]amino}methyl)benzoate from Ex. III and 140 μl (0.98 mmol) of methyl 5-bromovalerate in 3.3 ml of acetonitrile, and the mixture is heated at reflux for 48 hours. The mixture is then concentrated, taken up in ethyl acetate and washed with water. After drying over Na$_2$SO$_4$, filtration and concentration, the product is purified by column chromatography (silica gel, cyclohexane/ethyl acetate 5:1). This gives 389 mg (0.71 mmol, 78% yield) of a colorless oil.

R$_f$ (dichloromethane): 0.09. $^1$H-NMR (300 MHz, DMSO-d$_6$, δ/ppm): 7.87 (2H, d), 7.39 (2H, d), 7.30 (1H, t), 7.23 (2H, d), 7.04 (1H, m), 6.95–6.83 (4H, m), 3.82 (3H, s), 3.60 (5H, s), 3.55 (4H, m), 2.51 (1H, m partially obscured by DMSO), 2.19 (2H, t), 1.90–1.73 (7H, m), 1.70–1.53 (2H, m), 1.45–1.32 (5H, m). MS (ESI): 544 (M+H$^+$).

Ex. V

1-Bromo-4-[bromo(difluoro)methyl]benzene

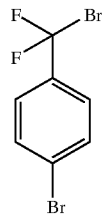

Under exclusion of oxygen, a solution of 14.0 g (67.63 mmol) of 1-bromo-4-(difluoromethyl)benzene (CAS 51776-71-7) and 25.3 g (142 mmol) of N-bromosuccinimide (NBS) in 190 ml of carbon tetrachloride is irradiated using a daylight lamp. During the radiation, the solvent reaches its boiling point. The mixture is irradiated under reflux for 24 hours. The mixture is then allowed to cool to room temperature, and precipitated succinimide is filtered off. Another 25 g of NBS are added to the filtrate, and the mixture is once more, under exclusion of oxygen, irradiated under reflux for 24 hours. After cooling, the mixture is again filtered and the filtrate is evaporated to dryness. This gives 18 g of a dark orange oil which is purified by vacuum distillation at 13 torr. This gives 12.7 g (44.4 mmol, 66% yield) of a colorless oil.

Boiling point (13 torr): 90–92° C. $^1$H-NMR (300 MHz, DMSO-$d_6$, δ/ppm): 7.79 (2H, d), 7.63 (2H, d). MS (ESI): 205/207 (M−Br$^-$).

Ex. VI

Methyl 4-({[2-(2-methoxyphenyl)ethyl]amino}methyl)benzoate

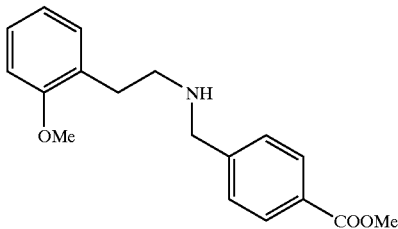

A solution of 92.08 g (0.597 mol) of 2-methoxyphenethylamine and 98.0 g (0.597 mol) of methyl 4-formylbenzoate in 2 l of ethanol is heated at reflux for 2 hours. The solvent is then removed under reduced pressure and the resulting residue is dissolved in 1 l of methanol. A total of 46.14 g of solid NaBH$_4$ are added a little at a time. After two hours of stirring at room temperature, the mixture is poured into water and extracted with ethyl acetate. The organic extract is washed with saturated sodium chloride solution and dried over Na$_2$SO$_4$. After filtration, the solvent is removed under reduced pressure. This gives 167.7 g (0.559 mol, 77% yield) of a colorless oil which is used without further purification for the next step. $^1$H-NMR (200 MHz, DMSO-$d_6$, δ/ppm): 7.90 (2H, d), 7.45 (2H, d), 7.17 (1H, t), 7.12 (1H, d), 6.92 (1H, d), 6.83 (1H, t), 3.83(3H, s), 3.78 (2H, s), 3.73 (3H, m), 2.75–2.63 (4H, m). MS (DCI, NH$_3$): 300 (M+H$^+$).

Ex. VII

Methyl 4-({[2-(2-hydroxyphenyl)ethyl]amino}methyl)benzoate hydrobromide

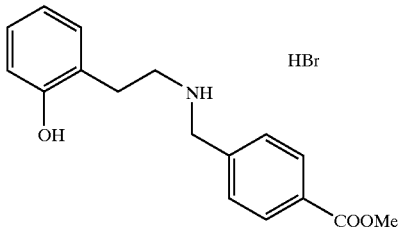

At 0° C., 661.4 ml (0.66 mol) of a 1-molar solution of boron tribromide in dichloromethane are added to a solution of 60.0 g (0.2 mol) of methyl 4-({[2-(2-methoxyphenyl)ethyl]amino}methyl)benzoate from Ex. VI in 200 ml of dichloromethane. The mixture is stirred at 0° C. for one hour. 300 ml of methanol are then added, and the mixture is heated at reflux for 18 hours. On cooling, the product precipitates out and is filtered off. Further product is obtained by concentrating the mother liquor. The collected product fractions are washed with ether. This gives 45.04 g (0.16 mol, 56% yield) of a white crystalline solid.

R$_f$(dichloromethane/methanol 10:1): 0.54. $^1$H-NMR (300 MHz, DMSO-$d_6$, δ/ppm): 9.58 (1H, broad), 9.02 (2H, broad), 8.03 (2H, d), 7.68 (2H, d), 7.09 (1H, d), 7.07 (1H, t), 6.82 (1H, d), 6.77 (1H, t), 4.29 (2H, s), 3.89 (3H, s), 3.18–3.10 (2H, m), 2.94–2.88 (2H, m). MS (ESI): 286 (M+H$^+$).

Ex. VIII

Methyl 4-{[[2-(2-hydroxyphenyl)ethyl](5-methoxy-5-oxopentyl)-amino]methyl}benzoate

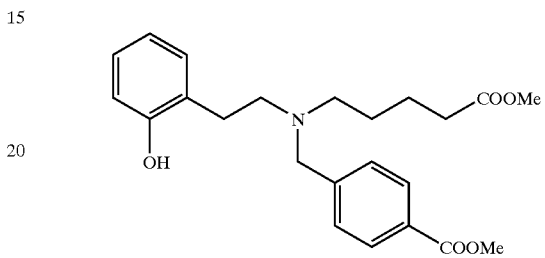

3.0 g (8.19 mmol) of methyl 4-({[2-(2-hydroxyphenyl)ethyl]amino}methyl)benzoate hydrobromide from Ex. VII, 1.3 ml (9.83 mmol) of methyl 5-bromovalerate and 1.74 g (16.38 mmol) of anhydrous sodium carbonate in 20 ml of acetonitrile are heated at reflux for three days. The mixture is then concentrated to dryness and the residue is taken up in ethyl acetate and washed with water and saturated sodium chloride solution. After drying over Na$_2$SO$_4$, the mixture is filtered and concentrated. The product is purified by flash chromatography (silica gel, cyclohexane/ethyl acetate 7:3). This gives 2.2 g (5.51 mmol. 67% yield) of a pale yellow oil.

R$_f$ (cyclohexane/ethyl acetate 2:1): 0.28. $^1$H-NMR (300 MHz, DMSO-$d_6$, δ/ppm): 9.57 (1H, s broad), 7.89 (2H, d), 7.43 (2H, d), 6.99 (1H, d), 6.98 (1H, t), 6.72 (1H, d), 6.67 (1H, t), 3.83 (3H, s), 3.69 (2H, s), 3.57 (3H, s), 2.71–2.66 (2H, m), 2.62–2.55 (2H, m), 2.45 (2H, t), 2.23 (2H, t), 1.51–1.40 (4H, m). MS (DCI, NH$_3$): 400 (M+H$^+$), 252.

Ex. IX

Methyl 4-{[(2-{2-[(4-bromophenyl)(difluoro)methoxy]phenyl}ethyl(5-methoxy-5-oxopentyl)amino]methyl}benzoate

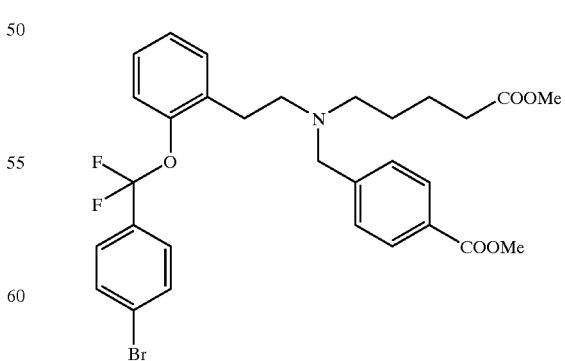

240 mg (6.0 mmol) of a 60% strength suspension of NaH in mineral oil are initially charged in 60 ml of anhydrous DMF, and at 0° C., a solution of 2.0 g (5.0 mmol) of methyl 4-{[[2-(2-hydroxyphenyl)ethyl](5-methoxy-5-oxopentyl)amino]methyl}benzoate from Ex. VIII in 1 ml of DMF is added. The mixture is allowed to warm to room temperature. After 30 minutes, 1.59 g (5.0 mmol) of 1-bromo-4-[bromo(difluoro)methyl]benzene from Ex. 5, dissolved in 1 ml of DMF, are added dropwise, and the mixture is heated at 70° C. After 15 hours, the mixture is allowed to cool to room temperature, diluted with dichloromethane and washed successively with aqueous 5% strength NaH$_2$PO$_4$ solution and saturated sodium chloride solution. Drying over Na$_2$SO$_4$. The product is purified by flash chromatography (silica gel, cyclohexane/ethyl acetate gradient 20:1→5:1). This gives 1.42 g (2.35 mmol, 47% yield) of a viscous yellow oil.

R$_f$ (cyclohexane/ethyl acetate 2:1): 0.39. $^1$H-NMR (300 MHz, DMSO-d$_6$, δ/ppm): 7.82 (2H, d), 7.76 (2H, d), 7.65 (2H, d), 7.33 (2H, d), 7.30–7.18 (4H, m), 3.86 (3H, s), 3.59 (2H, s), 3.57 (3H, s), 2.77 (2H, dd), 2.58 (2H, dd), 2.48 (2H, t), 2.14 (2H, t), 1.43–1.28 (4H, m). MS (DCI, NH$_3$): 604/606 (M+H$^+$).

Ex. X

Methyl 4-{[[(2-(2-difluoro[4'-(trifluoromethyl)-1,1'-biphenyl-4-yl]-methoxy}phenyl)ethyl](5-methoxy-5-oxopentyl)amino]methyl}benzoate

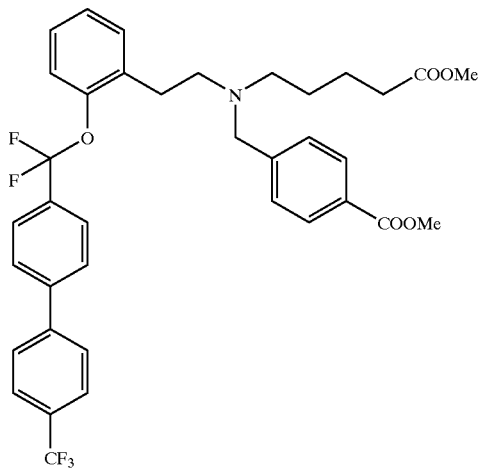

0.75 ml of a 2-molar aqueous sodium carbonate solution is added to a solution of 300 mg (0.50 mmol) of methyl 4-{[(2-{2-[(4-bromophenyl)(difluoro)methoxy]phenyl}ethyl(5-methoxy-5-oxopentyl)amino]methyl}benzoate from Ex. IX, 103.4 mg (0.55 mmol) of 4-trifluoromethylbenzeneboronic acid and 17.2 mg (0.01 mmol) of tetrakis(triphenylphosphino)palladium(0) in 5 ml of 1,2-dimethoxyethane, and the mixture is, under argon, heated at reflux for 18 hours. The mixture is then diluted with ethyl acetate and washed successively with 5% strength NaH$_2$PO$_4$ solution, water and saturated sodium chloride solution. Drying over Na$_2$SO$_4$. The product is purified by flash chromatography (silica gel, cyclohexane/ethyl acetate gradient 30:1→1:1). This gives 260 mg (0.39 mmol, 78% yield) of a yellow oil.

R$_f$ (cyclohexane/ethyl acetate 4:1): 0.28. $^1$H-NMR (300 MHz, DMSO-d$_6$, δ/ppm): 7.95–7.79 (10H, m), 7.37–7.19 (6H, m), 3.79 (3H, s), 3.60 (2H, s), 3.49 (3H, s), 2.81 (2H, dd), 2.61 (2H, dd), 2.40 (2H, t), 2.12 (2H, t), 1.41–1.30 (4H, m). MS (ESI): 670 (M+H$^+$).

Ex. XI

Methyl 2-[(4-cyclohexylphenoxy)methyl]-5-fluorobenzoate

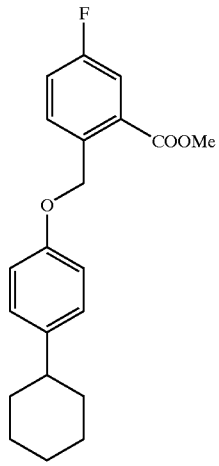

2.14 g (12.14 mmol) of 4-cyclohexylphenol and 3.0 g (12.14 mmol) of methyl 2-(bromomethyl)-5-fluorobenzoate (CAS 138786-65-9) are, together with 2.5 g (18.21 mmol) of anhydrous potassium carbonate, heated at reflux in 20 ml of acetonitrile. After three hours, the mixture is evaporated to dryness using a rotary evaporator. The residue is taken up in ether and washed successively with water and saturated sodium chloride solution. Drying is carried out over Na$_2$SO$_4$. The crude product is purified by flash chromatography (silica gel, cyclohexane/ethyl acetate 80:1). This gives 3.37 g (9.84 mmol, 81% yield) of a colorless oil.

R$_f$ (cyclohexane/ethyl acetate 9:1): 0.56. $^1$H-NMR (200 MHz, DMSO-d$_6$, δ/ppm): 7.72–7.43 (3H, m), 7.13 (2H, d), 6.88 (2H d), 5.32 (2H, s), 3.81 (2H, s), 2.51–2.36 (1H, m), 1.80–1.62 (5H, m), 1.46–1.20 (5H, m). MS (ESI): 707 (2M+Na$^+$), 365 (M+Na$^+$).

Ex. XII

{2-[(4-Cyclohexylphenoxy)methyl]-5-fluorophenyl}methanol

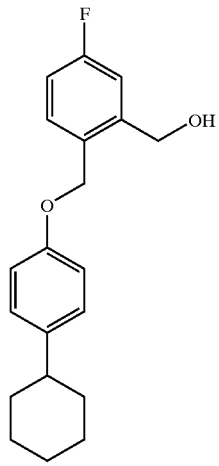

6.6 ml (6.6 mmol) of a 1-molar solution of LiAlH$_4$ in ether are initially charged and diluted with a further 20 ml of ether. Without cooling of the reaction flask, a solution of 3.2 g (9.35 mmol) of methyl 2-[(4-cyclohexylphenoxy)methyl]-5-fluorobenzoate from Ex. XI in 20 ml of ether is added dropwise such that the reaction mixture is just boiling. After 30 minutes, the reaction mixture is diluted with ether, and 20% strength aqueous potassium sodium tartrate solution is added carefully. The organic phase is separated off and washed successively with water and saturated sodium chloride solution. Drying over $Na_2SO_4$. After filtration and concentration using a rotary evaporator, 2.57 g (8.17 mmol, 87% yield) of product are obtained as a white solid.

$R_f$ (cyclohexane/ethyl acetate 9:1): 0.13. $^1$H-NMR (300 MHz, DMSO-$d_6$, δ/ppm): 7.45 (1H, dd), 7.27 (1H, dd), 7.12 (2H, d), 7.06 (1H, dt), 6.91 (2H, d), 5.31 (1H, t), 5.03 (2H, s), 4.60 (2H, d), 2.48–2.38 (1H, m), 1.80–1.66 (5H, m), 1.42–1.18 (5H, m). MS (DCI, $NH_3$): 646 (2M+$NH_4^+$), 332 (M+$NH_4^+$).

Ex. XIII 2-(Bromomethyl)-1-[(4-cyclohexylphenoxy)methyl]-4-fluorobenzene

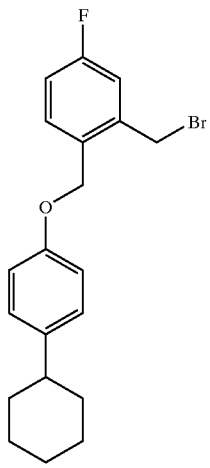

A solution of 2.5 g (7.95 mmol) of {2-[(4-cyclohexylphenoxy)methyl]-5-fluorophenyl-}methanol from Ex. XII in 30 ml of ether is added to a solution of 2.5 g (9.54 mmol) of triphenylphosphine and 3.2 g (9.54 mmol) of carbon tetrabromide in 30 ml of ether. After 20 hours of stirring at room temperature, a further 0.83 g of triphenylphosphine and 1.05 g of carbon tetrabromide solid are added. After six hours, the mixture is evaporated to dryness and the product is isolated by flash chromatography (silica gel, cyclohexane/ethyl acetate 50:1). This gives 2.3 g (6.1 mmol, 77% yield) of a colorless solid having low melting point.

$R_f$ (cyclohexane/ethyl acetate 9:1): 0.50. $^1$H-NMR (300 MHz, DMSO-$d_6$, δ/ppm): 7.52 (1H, dd), 7.39 (1H, dd), 7.20 (1H, dt), 7.15 (2H, d), 6.95 (2H, d), 5.17 (2H, s), 4.79 (2H, s), 2.50–2.39 (1H, m), 1.80–1.65 (5H, m), 1.42–1.18 (5H, m). MS (EI+): 376/378 (M$^+$).

Ex. XIV

{2-[(4-Cyclohexylphenoxy)methyl]-5-fluorophenyl}acetonitrile

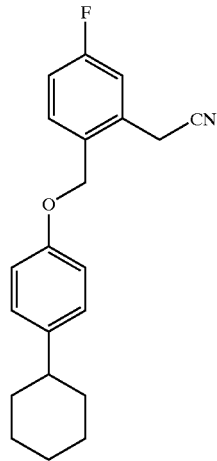

6 ml (5.96 mmol) of a 1-molar solution of tetra-n-butylammonium fluoride in THF is added to a solution of 0.8 ml (5.96 mmol) of trimethylsilyl cyanide in 5 ml of acetonitrile. After five minutes, a solution of 1.5 g (3.98 mmol) of 2-(bromomethyl)-1-[(4-cyclohexylphenoxy)methyl]-4-fluorobenzene from Ex. XIII in 5 ml of acetonitrile is added. The reaction mixture is stirred at room temperature for 30 minutes. The mixture is then evaporated completely using a rotary evaporator and the product is isolated by flash chromatography (silica gel, cyclohexane/ethyl acetate 20:1). This gives 1.15 g (3.56 mmol, 89% yield) of a white solid.

$R_f$ (cyclohexane/ethyl acetate 4:1): 0.53. $^1$H-NMR (300 MHz, DMSO-$d_6$, δ/ppm): 7.57 (1H, dd), 7.31 (1H, dd), 7.22 (1H, dt), 7.14 (2H, d), 6.95 (2H, d), 5.10 (2H, s), 4.11 (2H, s), 2.48–2.39 (1H, m), 1.80–1.66 (5H, m), 1.42–1.18 (5H, m). MS (DCI, $NH_3$): 664 (2M+$NH_4^+$), 358 (M+$NH_3$+$NH_4^+$), 341 (M+$NH_4^+$).

Ex. XV

2-{2-[(4-Cyclohexylphenoxy)methyl]-5-fluorophenyl}ethylamine

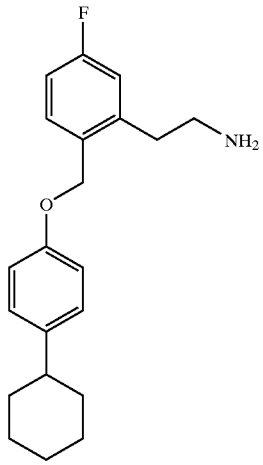

810 mg (2.50 mmol) of {2-[(4-cyclohexylphenoxy)methyl]-5-fluorophenyl}-acetonitrile from Ex. XIV are initially charged in 20 ml of anhydrous THF, and 2.53 ml (5.01 mmol) of a 2-molar solution of borane/dimethyl sulfide complex in THF are added. The mixture is heated at reflux for 2 hours. The mixture is then cooled, acidified using dilute hydrochloric acid and again briefly heated to reflux. The mixture is then once more allowed to cool and made alkaline using dilute aqueous sodium hydroxide solution. The mixture is extracted with ether. The organic phase is washed successively with water and saturated sodium chloride solution. Drying over $Na_2SO_4$. Filtration and concentration gives 820 mg (2.5 mmol, 100% yield) of a pale yellow oil which is used for the next step without further purification.

$R_f$ (ethyl acetate/methanol 7:3): 0.12. $^1$H-NMR (300 MHz, DMSO-$d_6$, δ/ppm): 7.45 (1H, dt), 7.15–7.00 (4H, m), 6.92 (2H, d), 5.02 (2H, s), 2.78–2.70 (4H, m), 2.50–2.40 (1H, m), 1.92 (2H, broad), 1.80–1.65 (5H, m), 1.42–1.20 (5H, m). MS (DCI, $NH_3$): 328 (M+H$^+$).

Ex. XVI

Methyl 4-{[(2-{2-[(4-cyclohexylphenoxy)methyl]-5-fluorophenyl}ethyl)amino]methyl}benzoate

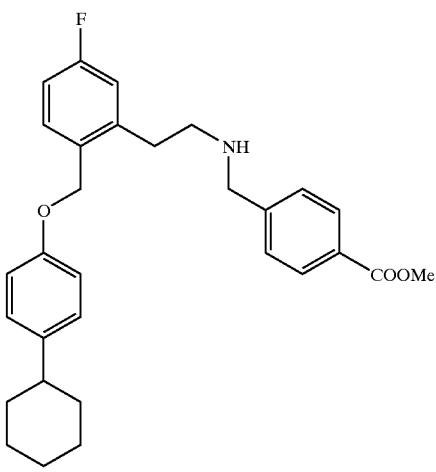

700 mg (2.14 mmol) of 2-{2-[(4-cyclohexylphenoxy)methyl]-5-fluorophenyl}ethylamine from Ex. XV and 316 mg (1.92 mmol) of methyl 4-formylbenzoate in 50 ml of toluene are boiled in a water separator for 30 minutes. The mixture is then concentrated by evaporation and the residue is taken up in 20 ml of methanol. With ice-cooling, 81 mg (2.14 mmol) of solid $NaBH_4$ are added a little at a time. The mixture is stirred at room temperature for 30 minutes. The mixture is then neutralized with 5% strength aqueous $NaH_2PO_4$ solution, diluted with water and extracted with ether. The organic phase is washed successively with water and saturated sodium chloride solution. Drying over $Na_2SO_4$. The product is isolated by flash chromatography (silica gel, cyclohexane/ethyl acetate 3:1). This gives 730 mg (1.53 mmol, 80% yield) of a colorless oil.

$R_f$ (cyclohexane/ethyl acetate 1:2): 0.40. $^1$H-NMR (300 MHz, DMSO-$d_6$, δ/ppm): 7.87 (2H, d), 7.45–7.39 (3H, m), 7.12–7.08 (3H, m), 7.02 (1H, dt), 6.85 (2H, d), 5.00 (2H, s), 3.83 (3H, s), 3.76 (2H, s), 2.83–2.70 (4H, m), 2.47–2.39 (1H, m), 1.74 (1H, s broad), 1.80–1.64 (5H, m), 1.39–1.18 (5H, m). MS (ESI): 476 (M+H$^+$).

Ex. XVII

Methyl 4-{[(2-{2-[(4-cyclohexylphenoxy)methyl]-5-fluorophenyl}ethyl)(5-methoxy-5-oxopentyl)amino]methyl}benzoate

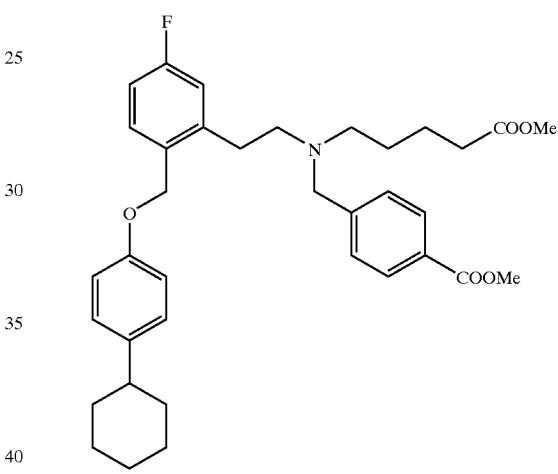

720 mg (1.51 mmol) of 4-{[(2-{2-[(4-cyclohexylphenoxy)methyl]-5-fluorophenyl}ethyl)amino]methyl}benzoate from Ex. XVI, 242 μl (1.82 mmol) of methyl 5-bromovalerate and 193 mg (1.82 mmol) of anhydrous sodium carbonate and 20 ml of butyronitrile are heated at reflux. After 48 hours, the mixture is concentrated by evaporation, taken up in ethyl acetate and washed successively with water and saturated sodium chloride solution. Drying over $Na_2SO_4$. The product is purified by flash chromatography (silica gel, cyclohexane/ethyl acetate 9:1). This gives 570 mg (0.97 mmol, 64% yield) of a colorless oil.

$R_f$ (cyclohexane/ethyl acetate 2:1): 0.56. $^1$H-NMR (300 MHz, DMSO-$d_6$, δ/ppm): 7.83 (2H, d), 7.42 (1H, dd), 7.37 (2H, d), 7.10 (2H, d), 7.08–6.99 (2H, m), 6.83 (2H, d), 4.93 (2H, s), 3.83 (3H, s), 3.62 (2H, s), 3.55 (3H, s), 2.80 (2H, dd), 2.63 (2H, dd), 2.48–2.37 (3H, m), 2.15 (2H, t), 1.80–1.65 (5H, m), 1.42–1.14 (9H, m). MS (ESI): 590 (M+H$^+$).

Synthesis Examples

Ex. 1

4-({(4-Carboxybutyl)[3-(4-cyclohexylphenoxy)benzyl]amino}methyl)benzoic acid

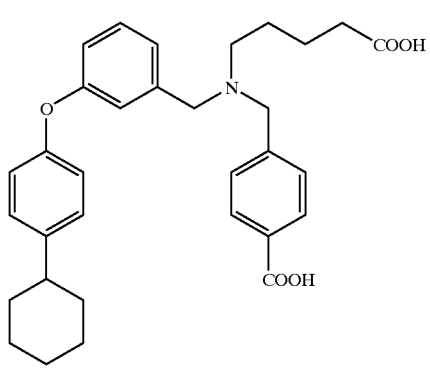

195 μl of a 45% strength solution of NaOH in water are added to a solution of 352 mg (0.65 mmol) of methyl 4-{[[3-(4-cyclohexylphenoxy)benzyl](5-methoxy-5-oxopentyl)amino]methyl}benzoate from Ex. IV in 3.5 ml of dioxane and 1.8 ml of water, and the mixture is stirred at 90° C. for 2 hours. After cooling, the dioxane is removed under reduced pressure and the aqueous phase is adjusted to pH 4–5 using 1-molar hydrochloric acid. This results in the precipitation of the product, which is filtered off, washed with water and dried. This gives 280 mg (0.54 mmol, 83% yield) of a white solid.

$R_f$ (ethyl acetate/methanol 7:3): 0.38. $^1$H-NMR (300 MHz, DMSO-d$_6$, δ/ppm): 12.49 (2H, broad s), 7.89 (2H, d), 7.47 (2H, d), 7.29 (1H, t), 7.20 (2H, d), 7.05 (1H, d), 6.98–6.80 (4H, m), 3.55 (2H, s), 3.50 (2H, s), 2.51 (1H, m partially obscured by DMSO), 2.41 (2H, m), 2.08 (2H, m), 1.89–1.62 (6H, m), 1.49–1.13 (8H, m). MS (ESI): 1030 (2M+H+), 516 (M+H$^+$).

The following compound was obtained in an analogous manner:

Ex. 3

4-({(4-Carboxybutyl)[3-(4-cyclohexylphenoxy)benzyl]amino}methyl)-benzoic acid hydrochloride

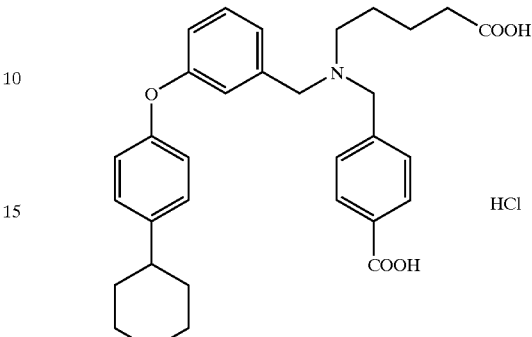

0.5 ml (2 mmol) of a 4-molar solution of HCl in dioxane is added to a solution of 220 mg (0.43 mmol) of 4-({(4-carboxybutyl)[3-(4-cyclohexylphenoxy)benzyl]amino}methyl)benzoic acid from Ex. 1 in 0.2 ml of dioxane, and the mixture is stirred at 60° C. for 1 h. The mixture is then concentrated by evaporation and the resulting colorless oil is repeatedly triturated with diethyl ether. The resulting crystals are filtered and dried. This gives 171 mg (0.31 mmol, 72% yield) of a white solid.

$R_f$ (ethyl acetate/methanol 7:3): 0.42. $^1$H-NMR (300 MHz, DMSO-d$_6$, δ/ppm): 12.50 (2H, broad s), 10.47 (1H, broad s), 7.99 (2H, d), 7.66 (2H, d), 7.49 (1H, t), 7.35 (1H, d), 7.25 (3H, d), 7.06 (1H, d), 6.95 (2H, m), 3.40 (2H, d) 3.45 (2H, d), 2.92 (2H, m), 2.51 (1H, m partially obscured by DMSO), 2.20 (2H, t), 1.89–1.62 (7H, m), 1.49–1.15 (7H, m). MS (ESI): 516 (M+H$^+$–HCl).

The following compounds are obtained in an analogous manner:

| Ex. | Formula | $^1$H-NMR δ[ppm](DMSO-d$_6$) |
|---|---|---|
| 2 (from 4-(4-trifluoromethyl-phenyl)-phenol | | 12.36(2H, broad), 7.79–7.69 (8H, m), 7.45–7.40(3H, m), 7.21–7.01(4H, m), 6.95(1H, d), 3.59(2H, s), 3.51(2H, s), 2.41–2.29(2H, m), 2.17–2.02 (2H, m), 1.55–1.34(4H, m). (300 MHz) |

| Ex. | Formula | $^1$H-NMR δ[ppm] (DMSO-$d_6$) |
|---|---|---|
| 4 (from 2) | 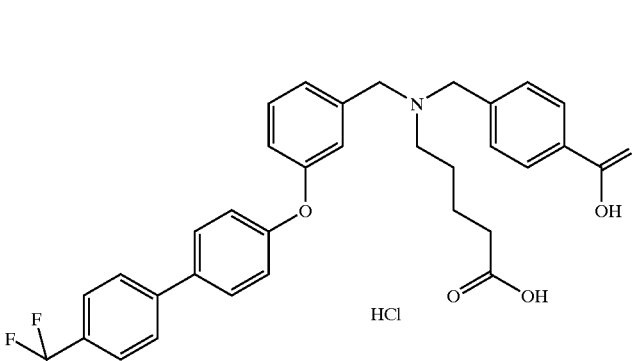 | 12.5(2H, broad), 10.45 (1H, broad), 7.96(2H, d), 7.88(2H, d), 7.84–7.72 (3H, m), 7.65(2H, d), 7.55–7.18(4H, m), 7.15 (2H, d), 6.93(1H, d), 4.43–4.28(4H, m), 3.02–2.88 (2H, m), 2.19(2H, t), 1.88–1.66(2H, m), 1.50–1.32(2H, m). (300 MHz) |
| 5 from 4-(4-fluoro-phenyl)-phenol | 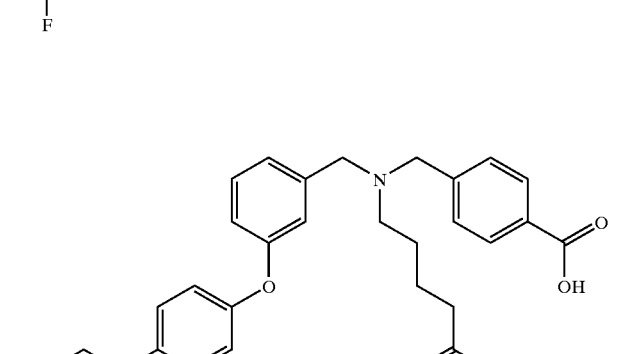 | 12.74(2H, broad), 10.79 (1H, broad), 7.97(2H, d), 7.78–7.57(6H, m), 7.53–7.02 (8H, m), 4.49–4.21 (4H, m), 3.02–2.80(2H, m), 2.20(2H, t), 1.88 (2H, m), 1.51–1.28(2H, m). (200 MHz) |

Ex. 6

4-({(4-Carboxybutyl)[2-(2-{difluoro[4'-(trifluoromethyl)-1,1'-biphenyl-4-yl]methoxy}phenyl)ethyl]amino}methyl)benzoic acid

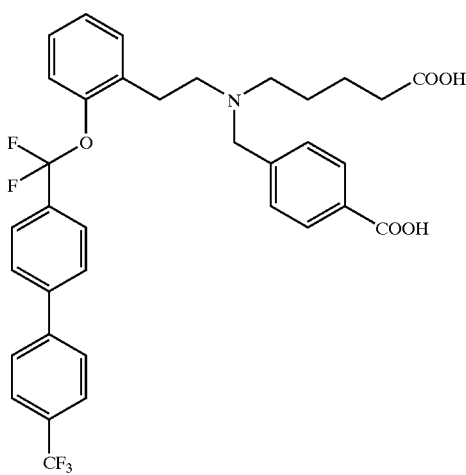

125 mg (0.19 mmol) of methyl 4-{[[(2-(2-difluoro[4'-(trifluoromethyl)-1,1'-biphenyl4-yl]methoxy}phenyl)ethyl](5-methoxy-5-oxopentyl)amino]methyl}-benzoate from Ex. X are heated at 60° C. in a mixture of 2 ml of THF, 1 ml of methanol and 3 ml of 2-molar aqueous LiOH solution for 1.5 hours. Most of the organic solvents are then removed using a rotary evaporator. The resulting aqueous solution is initially washed with ether and then adjusted to pH 4–5 using 1-molar hydrochloric acid. The mixture is extracted with ethyl acetate. The organic phase is dried over $Na_2SO_4$. Filtration and evaporation gives 107 mg of crude product which are purified by HPLC. The product fractions are combined and recrystallized from methanol. This gives 83 mg (0.13 mmol) of a white solid.

$R_f$ (ethyl acetate/methanol 7:3): 0.48. $^1$H-NMR (200 MHz, DMSO-$d_6$, δ/ppm): 12.38 (2H, broad), 7.98–7.77 (10H, m), 7.37–7.18 (6H, m), 3.59 (2H, s), 2.81 (2H, dd), 2.61 (2H, dd), 2.41 (2H, t), 2.08 (2H, t), 1.44–1.32 (4H, m). MS (ESI): 642 (M+H$^+$).

The following compounds were prepared in an analogous manner:

| Ex. | Formula | ¹H-NMR δ[ppm] (DMSO-d₆) |
|---|---|---|
| 7 (analogously to 6, but using benzene-boronic acid) | | 12.08(2H), 7.83–7.77 (6H, m), 7.71(2H, d), 7.52–7.41(3H, m), 7.37–7.18 (6H, m), 3.61(2H, s), 2.82(2H, m), 2.61 (2H, m), 2.42(2H, m), 2.08(2H, m), 1.40(4H, m). (300 MHz) |
| 8 (analogously to 6, but using 4-t-butyl-benzene-boronic acid) | | 12.22(2H, broad), 7.82–7.74 (6H, m), 7.63(2H, d), 7.51(2H, d), 7.33–7.28 (5H, m), 7.26–7.18 (1H, m), 3.60(2H, s), 2.81(2H, dd), 2.61(2H, dd), 2.41(2H, t), 2.09 (2H, t), 1.42–1.37(4H, m), 1.33(9H, s). (300 MHz) |
| 9 (analogously to 6, but using 4-chloro-benzene-boronic acid) | | 12.42(2H, broad), 7.87–7.72 (8H, m), 7.56(2H, d), 7.33–7.18(6H, m), 3.60(2H, s), 2.81(2H, dd), 2.60(2H, dd), 2.43–2.37 (2H, m), 2.12–2.04 (2H, m), 1.42–1.34(4H, m). (200 MHz) |

-continued

| Ex. | Formula | ¹H-NMR δ[ppm] (DMSO-d₆) |
|---|---|---|
| 10 (analogously to 6, but using 4-methoxy-benzene-boronic acid) |  | 12.40(2H, broad), 7.87–7.63 (8H, m), 7.39–7.20 (6H, m), 7.07(2H, d), 3.82(2H, s), 3.61(2H, broad), 2.82(2H, broad), 2.62(2H, broad), 2.41 (2H, broad), 2.10(2H, broad), 1.39(4H, broad). (200 MHz) |

Ex. 11

4-({(4-Carboxybutyl)[2-(2-{difluoro[-1,1'-biphenyl-4-yl]methoxy}phenyl)ethyl]amino}methyl)benzoic acid hydrochloride

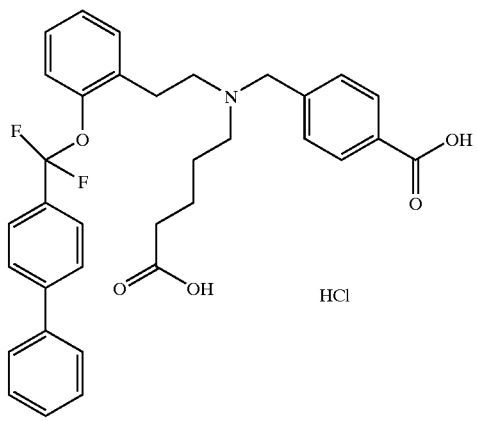

This compound was prepared from Ex. 7 analogously to Ex. 3.

¹H-NMR: δ [ppm] DMSO-d₆: 12.70 (2H, broad), 10.49 (1H, broad), 7.97 (2H, d), 7.83 (4H, s), 7.73–7.68 (4H, m), 7.57–7.29 (7H, m), 4.47 (2H, s broad), 3.20–3.15 (6H, m), 2.18 (2H, t), 1.79–1.63 (2H, m), 1.52–1.49 (2H, m). (200 MHz)

Ex. 12

4-{[(4-Carboxybutyl)(2-{2-[(4-cyclohexylphenoxy)methyl]-5-fluorophenyl}ethyl)amino]methyl}benzoic acid

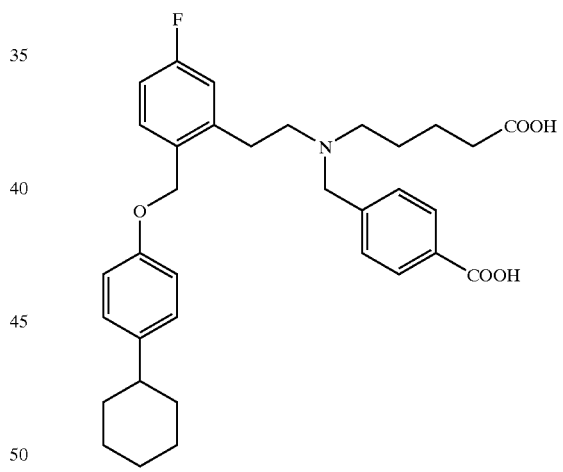

500 mg (0.85 mmol) of methyl 4-{[(2-{2-[(4-cyclohexylphenoxy)methyl]-5-fluorophenyl} ethyl)(5-methoxy-5-oxopentyl) amino]methyl} benzoate from Ex. XVII are dissolved in 5 ml of THF, and 20 ml of 2-molar aqueous sodium hydroxide solution are added. The mixture is heated at 50–60° C. for 15 hours. After cooling, the mixture is extracted with ether and the aqueous phase is then adjusted to pH 4–5 using 2-molar hydrochloric acid. The product precipitates in the form of a white solid which is filtered off with suction and washed with water. This gives 420 mg (0.75 mmol, 88% yield).

Melting point: >250° C.

$R_f$ (ethyl acetate/methanol 7:3): 0.43. $^1$H-NMR (300 MHz, DMSO-d$_6$, δ/ppm): 12.52 (2H, broad), 7.81 (2H, d), 7.42 (1H, dd), 7.27 (2H, d), 7.11 (2H, d), 7.08–6.98 (2H, m), 6.84 (2H, d), 4.93 (2H, s), 3.59 (2H, s), 2.79 (2H, dd), 2.63 (2H, dd), 2.48–2.37 (3H, m), 2.11–2.04 (2H, m), 1.79–1.63 (5H, m), 1.41–1.16 (9H, m). MS (ESI): 562 (M+H$^+$).

The following compounds were obtained in an analogous manner:

| Ex. | Formula | Analytical data |
|---|---|---|
| 13 (analogously to 12, but using 4-t-butyl-phenol) | | Melting point(° C.): >250 MS(ESI): 536(M + H$^+$) |
| 14 (analogously to 12, but using 4-(4-fluoro-phenyl)phenol) | | $^1$H-NMR(300MHz): δ [ppm]: (DMSO-d$_6$): 12.19 (2H, broad), 7.83(2H, d), 7.67–7.61(2H, m), 7.57 (2H, d), 7.47(1H, dd), 7.35 (2H, d), 7.27(2H, dd), 7.10–7.02(4H, m), 5.03 (2H, s), 3.63(2H, s), 2.82 (2H, dd), 2.66(2H,dd), 2.43(2H, 2.11(2H, 1.40 (4H) |
| 15 (analogously to 12, but using 4-(4-methoxy-phenyl-phenol) | | $^1$H-NMR(300MHz): δ [ppm]: (DMSO-d$_6$): 12.49 (2H, broad), 7.83(2H, d), 7.53(2H, d), 7.52(2H, d), 7.47(1H, dd), 7.33(2H, d), 7.09–6.97(6H, m), 5.02 (2H, s), 3.78(3H, s), 3.63 (2H, s), 2.82(2H, dd), 2.66 (2H,dd), 2.43(2H, pseudo-t), 2.11(2H, pseudo-t), 1.41 (4H). |

-continued

| Ex. | Formula | Analytical data |
|---|---|---|
| 16 (analogously to 12, but using 4-(4-chlorophenyl)-phenol) | | 12.38(2H, broad), 7.83 (2H, d), 7.64(2H, d), 7.60 (2H, d), 7.50–7.47(3H, m), 7.36(2H, d), 7.10–7.02(4H, m), 5.05(2H, s), 3.63(2H), 2.82(2H), 2.66(2H), 2.43 (2H), 2.10(2H), 1.41(4H). (300 MHz) |
| 17 (analogously to 12, but using 4-(4-trifluoromethylphenyl)-phenol) | | 12.40(2H, broad), 7.87–7.74 (6H, m), 7.68(2H, d), 7.48(1H, dd), 7.33(2H, d), 7.10–7.00(4H, m), 5.07 (2H, s), 3.63(2H, s), 2.82 (2H, dd), 2.68(2H, dd), 2.43(2H), 2.11(2H), 1.41 (4H). (200 MHz) |
| 18 (analogously to 12, but using 4-(4-cyanophenyl)phenol) | | 12.32(2H, broad), 7.91–7.80 (6H, m), 7.71(2H, d), 7.48(1H, dd), 7.34(2H, d), 7.09–7.00(4H, m), 5.07 (2H, s), 3.64(2H, s), 2.82 (2H), 2.67(2H), 2.43(2H), 2.10(2H), 1.40(4H). (200 MHz) |

-continued

| Ex. | Formula | Analytical data |
|---|---|---|
| 19 (analogously to 12, but using 4-(4-trifluoromethylphenyl) phenol and methyl 2-bromo-methyl-benzoate) | | 12.39(2H, broad), 7.87–7.74 (6H, m), 7.68(2H, d), 7.44–7.33(3H, m), 7.29–7.17 (3H, m), 7.07(2H, d), 5.07(2H, s), 3.66(2H, s), 2.82(2H, dd), 2.66(2H, dd), 2.45(2H, partially obscured by DMSO), 2.11 (2H), 1.42(4H). (200 MHz) |
| 20 (analogously to 12, but using 4-(4-methoxyphenyl)phenol and methyl 2-bromo-methyl-benzoate) | | 12.37(2H, broad), 7.83 (2H, d), 7.53(2H, d), 7.52 (2H, d), 7.42–7.37(3H, m), 7.30–7.19(3H, m), 6.98 (4H, d), 5.04(2H, s), 3.78 3H, s), 3.65(2H, s), 2.81 (2H, dd), 2.64(2H,dd), 2.45(2H, partially obscured by DMSO), 2.11(2H), 1.42 (4H). (300 MHz) |
| 21 (analogously to 12, but using 4-(4-chlorophenyl) phenol and methyl 2-bromo-methyl-benzoate) | | 12.39(2H, broad), 7.82 (2H, d), 7.63(2H, d), 7.59 (2H, d), 7.49–7.34(5H, m), 7.28–7.17(3H, m), 7.02 (2H, d), 5.07(2H, s), 3.65 (2H, s), 2.80(2H, dd), 2.63 (2H, dd), 2.45(2H, partially obscured by DMSO), 2.11 (2H), 1.42(4H). (200 MHz) |

What is claimed is:

1. A compound of the general formula (I)

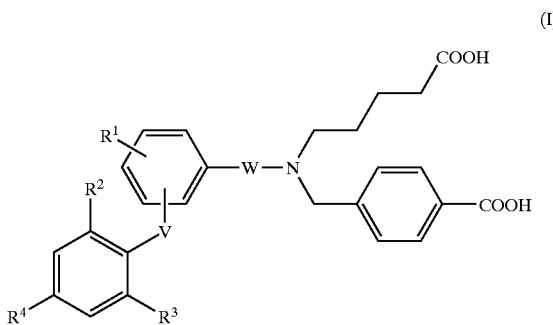

in which
R$^1$ is located in the meta- or para-position to the radical W and represents a radical selected from the group consisting of H, halogen and OCF$_3$;
R$^2$ represents H, or halogen;
R$^3$ represents H or halogen;
R$^4$ represents C$_{1-6}$-alkyl, C$_{3-8}$-cycloalkyl, CF$_3$, OCF$_3$, F, Cl, OMe or phenyl, where the phenyl radical may additionally carry a substituent selected from the group consisting of halogen, CN, C$_{1-6}$-alkoxy, CF$_3$, C$_{1-6}$-alkyl;
V is located in the ortho- or meta-position to the radical W and represents O, CH$_2$O, OCF$_2$ or O—C$_{1-6}$-alkyl-O;
W represents CH$_2$ or CH$_2$CH$_2$;
or a pharmaceutically acceptable salt or stereoisomer thereof.

2. The compound as claimed in claim 1, wherein
R$^1$ is located in the meta-position to the radical W and represents H or halogen;
R$^2$ represents H or halogen;
R$^3$ represents H or halogen;
R$^4$ represents C$_{1-6}$-alkyl, C$_{3-8}$-cycloalkyl or phenyl, where the phenyl radical may additionally carry a substituent selected from the group consisting of halogen, CN, C$_{1-6}$-alkoxy, CF$_3$, C$_{1-6}$-alkyl;
V is located in the ortho- or meta-position to the radical W and represents O, CH$_2$O, OCF$_3$ or O—C$_{1-6}$-alkyl-O;
W represents CH$_2$ or CH$_2$CH$_2$;
or a pharmaceutically acceptable salt or stereoisomer thereof.

3. The compound as claimed in claim 1, wherein
R$^1$ is located in the meta-position to the radical W and represents a radical selected from the group consisting of H, F, Cl and Br;
R$^2$ represents H,
R$^3$ represents H;
R$^4$ represents methyl, ethyl, n-propyl, i-propyl, n-butyl, i-butyl, t-butyl, cyclopropyl, cyclobutyl, cyclopentyl, cyclohexyl, or phenyl, where the phenyl radical may additionally carry a substituent from the group consisting of F, Cl, Br, CN, methoxy, ethoxy, n-propoxy, i-propoxy, n-butyloxy, i-butyloxy, t-butyloxy, CF$_3$, methyl, ethyl, n-propyl, i-propyl, n-butyl, i-butyl, t-butyl;
V is located in the ortho- or meta-position to the radical W and represents O, CH$_2$O, OCF$_2$ or O—C$_{1-6}$-alkyl-O;
W represents CH$_2$ or CH$_2$CH$_2$;
or a pharmaceutically acceptable salt or stereoisomer thereof.

4. The compound as claimed in claim 1, wherein
R$^1$ is located in the meta-position to the radical W and represents H;
R$^2$ represents H;
R$^3$ represents H;
R$^4$ represents cyclopropyl, cyclobutyl, cyclopentyl, cyclohexyl, or phenyl, where the phenyl radical may additionally carry a substituent from the group consisting of F, Cl, Br, CF$_3$;
V is located in the meta-position to the radical W and represents O;
W represents CH$_2$;
or a pharmaceutically acceptable salt or stereoisomer thereof.

5. The compound as claimed in claim 1, characterized in that wherein
R$^1$ is located in the meta-position to the radical W and represents H;
R$^2$ represents H;
R$^3$ represents H;
R$^4$ represents phenyl, where the phenyl radical may additionally carry a substituent from the group consisting of F, Cl, Br, OMe, CF$_3$, methyl, ethyl, n-propyl, i-propyl, n-butyl, i-butyl, t-butyl;
V is located in the ortho-position to the radical W and represents OCF$_2$;
W represents CH$_2$CH$_2$;
or a pharmaceutically acceptable salt or stereoisomer thereof.

6. The compound as claimed in claim 1, wherein
R$^1$ is located in the meta-position to the radical W and represents a radical selected from the group consisting of H, F, Cl and Br;
R$^2$ represents H;
R$^3$ represents H;
R$^4$ represents methyl, ethyl, n-propyl, i-propyl, n-butyl, i-butyl, t-butyl, cyclopropyl, cyclobutyl, cyclopentyl, cyclohexyl, or phenyl, where the phenyl radical may additionally carry a substituent selected from the group consisting of F, Cl, Br, CN, OMe, CF$_3$, methyl, ethyl, n-propyl, i-propyl, n-butyl, i-butyl, t-butyl;
V is located in the ortho-position to the radical W and represents CH$_2$O;
W represents CH$_2$CH$_2$;
or a pharmaceutically acceptable salt or stereoisomer thereof.

7. A process for preparing compounds of the general formula (I), comprising the following steps:
compounds of the formula (II)

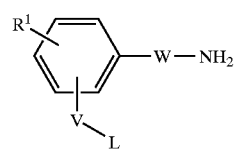

in which

R¹, V and W are as defined in claim 1 and

L, if V is O, represents methyl or otherwise represents a radical of the formula

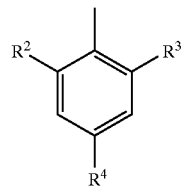
(II-A)

where R², R³ and R⁴ are as defined in claim 1, with a $C_{1-6}$-alkyl 4-formylbenzoate in an organic solvent, to give a compound of the formula (III)

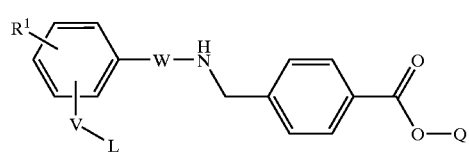
(III)

in which R¹, V, W and L are as defined above and Q represents a $C_{1-6}$-alkyl radical, then reacting with a $C_{1-6}$-alkyl ω-halovalerate in an organic solvent in the presence of a base with heating to give compounds of the formula (IV)

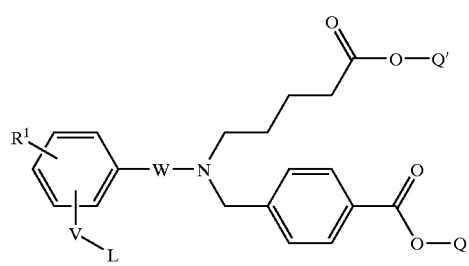
(IV)

in which R¹, V, W, and Q are as defined above, Q' represents a $C_{1-6}$-alkyl radical and L represents H— if V is O— or a radical of the formula II-A, then—if V is O and L represents H—reacting the compound of the formula (IV) with a compound of the formula IV-A in an organic solvent with heating

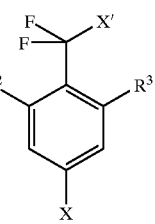
(IV-A)

where R² and R³ are as defined in claim 1 and X and X' each represent halogen, followed by palladium-catalyzed substitution of the radical X with a benzene boronic acid derivative to give compounds of the formula (V)

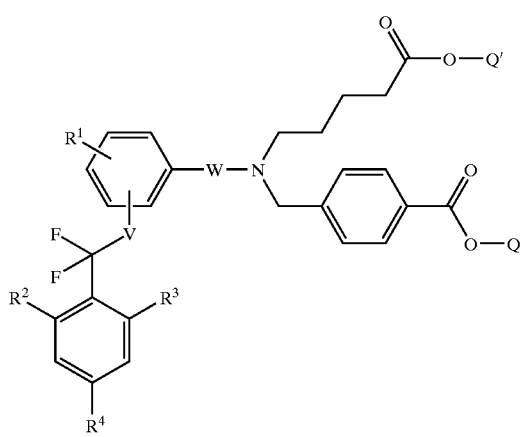
(V)

and subsequent hydrolysis of the compounds of the formula (IV) or (V) under alkaline conditions to give the compounds of the formula (I).

8. The process of claim 7 wherein the step of reacting the compound of formula (II) with a $C_{1-6}$-alkyl 4-formylbenzoate is carried out with heating and simultaneous or subsequent addition of a reducing agent.

9. The process of claim 7 wherein in the step of reacting the compound of formula (III) with a $C_{1-6}$-alkyl ω-haolvalerate, the compound of formula (III) is first subjected to prior cleavage of the ether to give the free hydroxyl group, if V represents O and L represents methyl.

10. A pharmaceutical composition comprising a compound according to claim 1 and a pharmaceutically acceptable carrier.

11. A method for treating a cardiovascular disorder selected from angina pectoris, ischemias, hypertension, and arteriosclerosis comprising administering to a subject in need thereof an effective amount of a compound of claim 1.

12. A method for treating fibrosis of the liver comprising administering to a subject in need thereof an effective amount of a compound of claim 1.

* * * * *